(12) United States Patent
Adams (10) Patent No.: US 7,458,956 B1
(45) Date of Patent: Dec. 2, 2008

(54) APPARATUS FOR DELIVERY OF CONTROLLED DOSES OF THERAPEUTIC DRUGS IN ENDOLUMINAL PROCEDURES

(75) Inventor: Ronald David Adams, Holliston, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 09/432,579

(22) Filed: Nov. 12, 1999

(51) Int. Cl.
*A61M 5/178* (2006.01)
(52) U.S. Cl. ..................................................... 604/158
(58) Field of Classification Search ............ 604/80–83, 604/218, 236, 523, 164.01, 141–143, 154–155, 604/93.01, 131, 145, 147, 151, 164.02, 181, 604/187, 191, 207, 212, 237, 21, 22, 27, 604/44, 158, 95.01, 95.02, 506–509; 607/120; 128/899
See application file for complete search history.

(56) References Cited

U.S. PATENT DOCUMENTS

| 3,964,139 | A | * | 6/1976 | Kleinmann et al. ........... 24/506 |
| 3,993,065 | A | | 11/1976 | Szabo et al. |
| 4,198,975 | A | * | 4/1980 | Haller ........................ 604/157 |
| 4,578,061 | A | * | 3/1986 | Lemelson ............. 604/170.01 |
| 4,666,430 | A | * | 5/1987 | Brown et al. ................. 604/141 |
| 4,790,819 | A | | 12/1988 | Li et al. |
| 4,900,303 | A | * | 2/1990 | Lemelson .................... 604/11 |
| 4,915,688 | A | * | 4/1990 | Bischof et al. ................. 604/83 |
| 4,969,874 | A | * | 11/1990 | Michel et al. ............... 604/140 |
| 5,186,431 | A | | 2/1993 | Tamari |
| 5,244,461 | A | * | 9/1993 | Derlien ........................ 604/65 |
| 5,306,246 | A | | 4/1994 | Sahatjian et al. |
| 5,334,170 | A | * | 8/1994 | Moroski ....................... 604/80 |
| 5,356,375 | A | * | 10/1994 | Higley ......................... 604/80 |
| 5,358,493 | A | | 10/1994 | Schweich, Jr. et al. |
| 5,391,183 | A | | 2/1995 | Janzen et al. |
| 5,437,631 | A | | 8/1995 | Janzen |
| 5,503,627 | A | * | 4/1996 | McKinnon et al. ........... 604/72 |
| 5,505,709 | A | * | 4/1996 | Funderburk et al. ......... 604/155 |
| 5,522,804 | A | * | 6/1996 | Lynn .......................... 604/191 |
| 5,545,133 | A | | 8/1996 | Burns et al. |
| 5,558,642 | A | | 9/1996 | Schweich, Jr. et al. |
| 5,599,303 | A | * | 2/1997 | Melker et al. ................. 604/80 |
| 5,649,959 | A | | 7/1997 | Hannam et al. |
| 5,702,384 | A | | 12/1997 | Umeyama |
| 5,746,728 | A | | 5/1998 | Py |
| 5,766,157 | A | | 6/1998 | Tilton, Jr. |

(Continued)

FOREIGN PATENT DOCUMENTS

EP 0 202 658 4/1989

(Continued)

OTHER PUBLICATIONS

International Search Report for Application No. PCT/US 00/ 28142 filed Oct. 12, 2000.

*Primary Examiner*—Kevin C. Sirmons
*Assistant Examiner*—Catherine N Witczak
(74) *Attorney, Agent, or Firm*—Kenyon & Kenyon LLP (57) ABSTRACT

An improved method and apparatus for administering drugs during an endoluminal procedure is disclosed. An embodiment of the present invention utilizes a catheter having distal and proximal ends and a drug reservoir located within the catheter to efficiently and accurately deliver drugs during an endoluminal procedure.

5 Claims, 6 Drawing Sheets

U.S. PATENT DOCUMENTS

| | | | |
|---|---|---|---|
| 5,772,629 A | 6/1998 | Kaplan | |
| 5,807,311 A | 9/1998 | Palestrant | |
| 5,807,337 A | 9/1998 | Yamada et al. | |
| 5,820,610 A | 10/1998 | Baudino | |
| 5,833,658 A | 11/1998 | Levy et al. | |
| 5,840,061 A * | 11/1998 | Menne et al. | 604/68 |
| 5,845,646 A * | 12/1998 | Lemelson | 128/899 |
| 5,997,509 A * | 12/1999 | Rosengart et al. | 604/164.01 |
| 6,004,295 A * | 12/1999 | Langer et al. | 604/164.01 |
| 6,050,986 A | 4/2000 | Hektner | |
| 6,056,716 A * | 5/2000 | D'Antonio et al. | 604/68 |
| 6,099,511 A * | 8/2000 | Devos et al. | 604/246 |
| 6,200,289 B1 * | 3/2001 | Hochman et al. | 604/67 |
| 6,245,046 B1 * | 6/2001 | Sibbitt | 604/191 |
| 6,299,603 B1 * | 10/2001 | Hecker et al. | 604/181 |
| 6,322,536 B1 * | 11/2001 | Rosengart et al. | 604/164.01 |
| 6,595,958 B1 * | 7/2003 | Mickley | 604/164.01 |

FOREIGN PATENT DOCUMENTS

WO      WO 98/10824      3/1998

* cited by examiner

FIG. 1
(Previously Known)

APPARATUS FOR DELIVERY OF CONTROLLED DOSES OF THERAPEUTIC DRUGS IN ENDOLUMINAL PROCEDURES

FIELD OF THE INVENTION

This invention generally relates to endoluminal procedures. More specifically it relates to an improved method and apparatus for providing accurate, easy to administer, minimum waste delivery of therapeutic drugs while performing endoluminal procedures.

BACKGROUND

An endoluminal procedure is a medical procedure that takes place in one of the many lumens within the human body. An endoluminal procedure may take place in vascular, gastrointestinal, or air exchange lumens, and may involve disease diagnosis, or treatment, or both. Millions of endoluminal procedures are performed each year in hospitals around the world.

Figure 1:
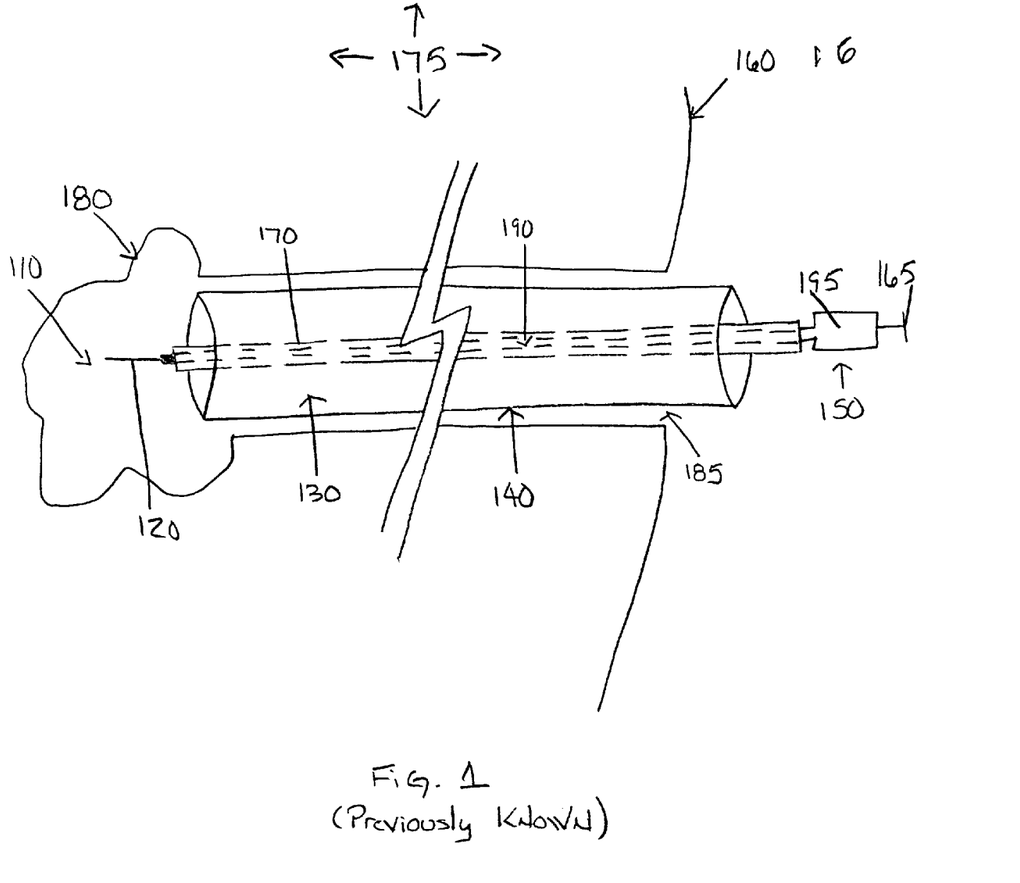
FIG. 1 illustrates a known drug delivery device wherein the drug reservoir is located at the proximal end of the catheter.

Endoluminal procedures are often performed utilizing a device known as an endoscope. With reference to FIG. 1, an endoscope 140 is a tube, either rigid or flexible, which is introduced into the body lumen 180 through an opening in the human body 185, such as the mouth or rectum. The endoscope may simply be used to hold open the lumen for examination or it can and usually will contain an open or "working" channel 130 into which the Endoscopist will insert and withdraw a myriad of endoluminal devices. Lights, visionary systems, and other devices may be incorporated into or used in conjunction with the endoscope to assist in completing the endoluminal procedure.

A treatment device that is commonly used during the completion of endoluminal procedures is a catheter. As illustrated in FIG. 1, the catheter 170 is essentially a flexible hollow tube. Often the catheter is fitted with a hypodermic needle 120 fitted to its distal end for the injection of therapeutic or diagnostic agents. In certain applications, where therapeutic drugs are to be passed into the body lumen 180, the catheter 170 will accept, or be manufactured with, a syringe 150 at its proximal end. The syringe 150 can be pre-filled with a therapeutic drug 195 or it can be filled at some other time, for example, contemporaneous with the endoluminal procedure being performed.

The endoscope 140 will be positioned to allow access to the treatment area 110. Then, as required, the Endoscopist will position the distal end of the catheter through the endoscope into the treatment area 110. The positioning of the catheter is often a difficult and time-consuming process as it must be done by the Endoscopist from the proximal end of the endoscope, which may be a hundred or more centimeters from the treatment area. Once the catheter is positioned drugs can be administered or some other procedure can be performed. Administering the drugs can be an arduous task due to the tremendous pressure required to be applied to the handle 165 to force the drug out of the syringe 150, through the entire length of the catheter 170 and ultimately out the hypodermic needle 120. This is particularly true when the therapeutic drug to be administered is highly viscous.

This method is highly inefficient as the entire internal channel 190 of the catheter 170 must be filled with the drug before even a small amount can be forced into the treatment area 110. Moreover, since the entire internal channel 190 of the catheter 170 will be filled with the drug, a large amount of the drug is simply disposed of, along with the catheter, at the completion of the procedure. This unwanted disposal of therapeutic drugs can be expensive and can add significant cost to the procedure.

Thus, it would be desirable to provide an apparatus that can accurately deliver a therapeutic drug to an endoluminal treatment site both efficiently and with a minimum of effort and waste.

SUMMARY OF THE INVENTION

The present invention is an improved method and apparatus for administering drugs during an endoluminal procedure that includes a catheter having a distal end and a proximal end and a drug reservoir located within the catheter to efficiently and accurately deliver drugs during an endoluminal procedure.

DETAILED DESCRIPTION

Figure 2:
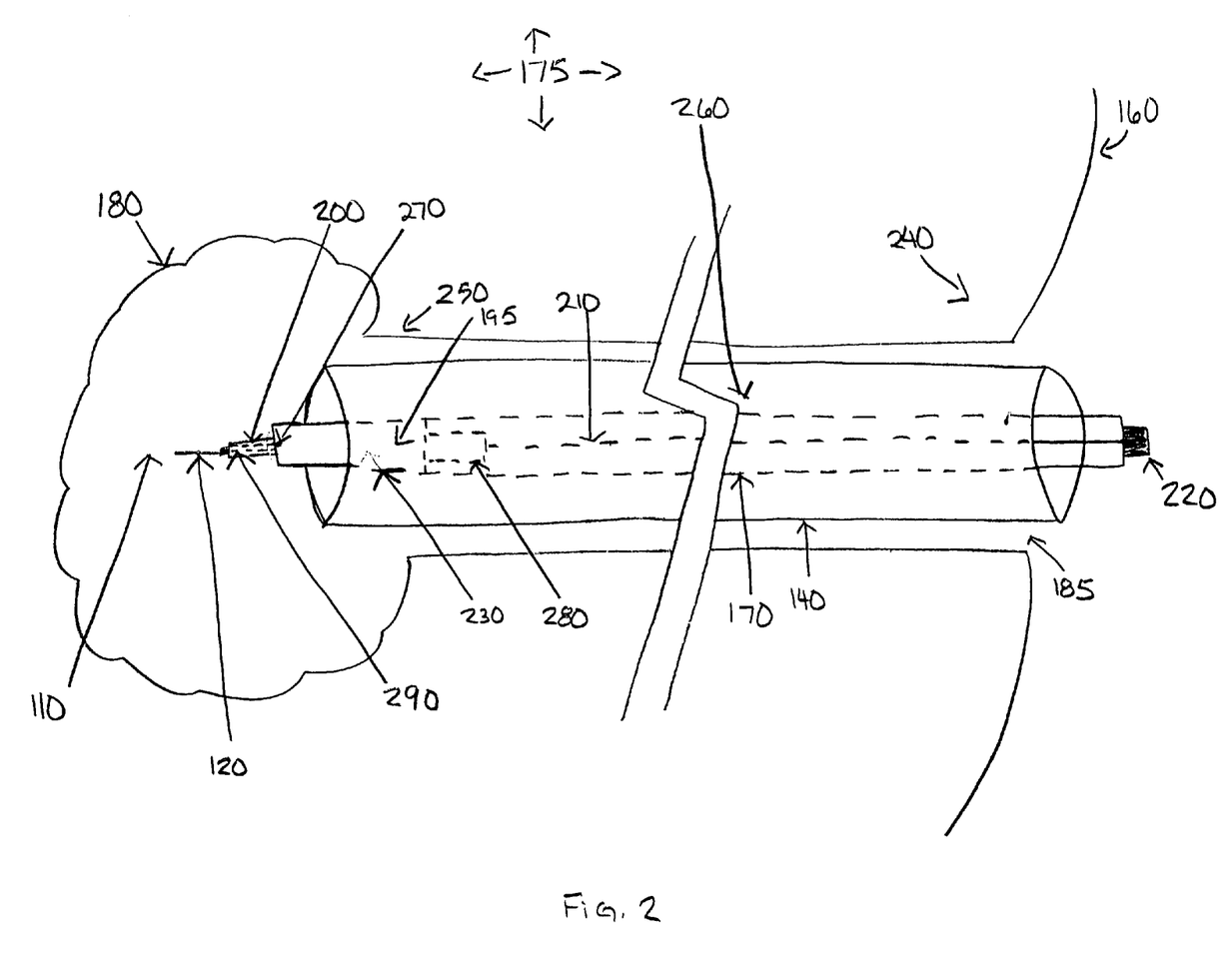
FIG. 2 illustrates a catheter, in accordance with an embodiment of the present invention, as it would appear having been introduced into a lumen of the body through the working channel of an endoscope.

The instant invention provides for an efficient and effective method and apparatus for delivering therapeutic drugs to an endoluminal cavity. FIG. 2 illustrates an embodiment of the drug delivery device 260. As can be seen, the drug delivery device 260 is comprised of a hypodermic needle 120, a connection tube 200, a drug reservoir 230, a flexible catheter 170, an activation line 210, an activation mechanism 280, and an activation mechanism switch 220. The hypodermic needle 120 is rigidly connected to one end of the hollow connection tube 200 and is in fluid communication with the connection tube channel 290 of the hollow connection tube 200. The hollow connection tube 200 is a rigid member capable of withstanding the bending and kinking forces generated during the insertion, manipulation, and use of the drug delivery device 260 and is generally less than one centimeter in length. The hollow connection tube 200 is rigidly and sealably connected to the cylindrically shaped drug reservoir 230. The exit orifice 270 of the drug reservoir 230 is aligned with, and in fluid communication with, the connection tube channel 290. An activation mechanism 280 is rigidly connected to the proximal end of the drug reservoir 230 and is in communication with the drugs 195 present in drug reservoir 230. The activation mechanism 280 generates the compressive force necessary to eject drugs 195 from the drug reservoir 230 through the exit orifice 270, through the connection tube channel 290, and out the hypodermic needle 120. The activation mechanism is connected to a wire 210 which is connected to an activation mechanism control switch 220. The activation mechanism control switch 220 is operated by the Endoscopist and turns the activation mechanism 280 on and off.

The drug 195 in FIG. 2 can be pre-loaded by the drug manufacturer into the drug reservoir 230 or can be loaded by the Endoscopist at a time contemporaneous with the procedure. To fill the drug reservoir 230, the Endoscopist would load the drug 195 into the drug reservoir 230 by unscrewing the drug reservoir 230 from the distal end of the catheter 170, filling the drug reservoir 230 with a desired dose of drug 195 through the exit orifice 270 and rescrewing the drug reservoir 230 back into the distal end of the catheter 170.

The drug agents used in the present invention include, for example: pharmaceutically active compounds, biologically active solutions, proteins, oligonucleotides, genes, DNA compacting agents, gene/vector systems (i.e., anything that allows for or enhances the uptake and expression of nucleic acids), nucleic acids (including, for example, DNA, cDNA, RNA, antisense DNA or RNA), cells (autologous, allogenic, or xenogeneic), and liposomes and cationic polymers that are selected from a number of types depending on the desired application. Examples of the biologically active solutes include: anti-thrombogenic agents such as heparin, heparin derivatives, urokinase, and PPack (dextrophenylalanine proline arginine chloromethylketone); anti-proliferative agents such as paclitaxel, enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin, protaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogeneus vascoactive mechanisms.

In practicing the invention embodied in FIG. 2 the Endoscopist inserts the endoscope 140 into the patient's body 185 through the opening in the patient's body 185 until the distal end of the endoscope 140 provides access to the lumen 180 to be treated. The distal end of the drug delivery device 260, loaded with the requisite drug 195, is then guided by the Endoscopist towards the distal end of the endoscope 140 until the hypodermic needle 120 of the drug delivery device 260 reaches the treatment area 110 of the lumen 180. Navigation aides, common in the art, such as lights and optical cameras, typically provided by the endoscope, may be used to aid in the positioning of the distal end of the drug delivery device 260. Once properly positioned, the Endoscopist will engage the activation control mechanism 220 thereby sending a signal through the wire 210 to the activation mechanism 280 to instruct the activation mechanism 280 to urge the drug 195, present in the drug reservoir 230, through the hypodermic needle 120, and into the treatment area 110.

Once the drug 195 has been administered into the treatment area 110, the Endoscopist retracts the drug delivery device 260 from the endoscope 140 and discards the drug delivery device 260.

The activation mechanism 280 may have numerous alternative embodiments as will be evident to those of skill in the art. For example, an electric motor, a cable assembly, or compressed gas could be employed, in conjunction with a moveable face of the drug reservoir 230, to generate the force necessary to urge the drug 195 from the drug reservoir 230 during the procedure. Alternatively, a collapsible drug reservoir can be employed wherein the compressed gas is used to collapse or implode the drug reservoir 230 in order to squeeze the drug 195 from it as the volume of the drug reservoir 230 decreases.

In addition, a specific dosage of a drug can be administered through this process. For example, the Endoscopist can unscrew the drug reservoir 230 from the distal end of the catheter 170 before the procedure begins and load a specific dosage of a drug 195 into the drug reservoir 230 in order to completely expel it during the procedure. Alternatively, the specific dosage could be pre-measured by the manufacturer and then loaded into the drug reservoir 230 by the manufacturer. Moreover, the activation mechanism 280 could be calibrated in order to eject a predetermined drug dosage from the drug chamber each time the activation mechanism 280 is engaged.

Figure 3:
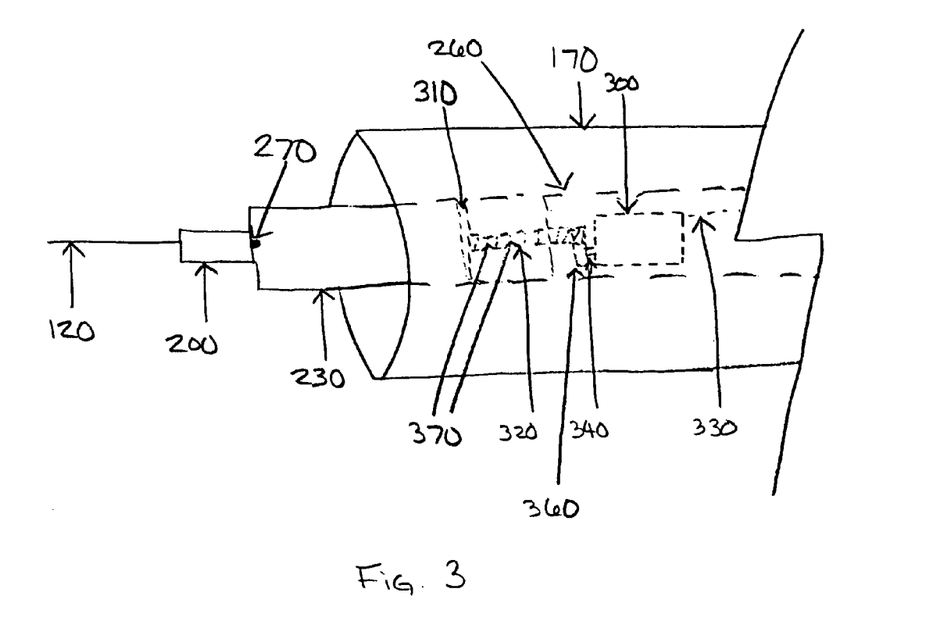
FIG. 3 illustrates the distal end of the catheter of FIG. 2 in accordance with an embodiment of the present invention.

FIG. 3 illustrates an alternative embodiment of a device that can be employed when practicing the present invention. FIG. 3 is an enlarged view of the distal end of the catheter 170. In FIG. 3 the activation mechanism 280 comprises an electric motor 300 having a rotating shaft 340, a gear 360, a connecting member 320, a piston 310, and motor control wires 330. As can be seen, the piston 310 comprises one wall of the cylindrically shaped drug reservoir 230 that is designed to slide within the drug reservoir 230 in order to push the drug 195 through the exit orifice 270 of the drug reservoir 230. The piston 310 is pushed by the connecting member 320. The connecting member 320 is rigid and pole-like with screw threads 370 etched into its outer surface. The electric motor shaft 340 is in contact with a gear 360 that is in communication with the screw threads 370 of the connecting member 320 and causes the connecting member 320 to push the piston 310 towards the drug 195 in the drug reservoir 230 when the electric motor 300 is in operation. The greater the number of rotations completed by the electric motor 300 the greater the distance the piston 310 will travel and the greater the volume of drug 195 will be forced from the drug reservoir 230 and out the hypodermic needle 120.

The electric motor 300 in FIG. 3 is activated by the Endoscopist from the proximal end of the drug delivery device 260. As required, the Endoscopist will energize the motor control wires 330 by depressing the activation mechanism control switch 220 which contains both a depressable on and off button and a common 1.5 volt dc power source such a Duracell® MS76 silver oxide battery or an Energizer® 357 watch battery. Once activated, the electric motor 300 in FIG. 3 will rotate, ultimately pushing the piston 310 forward into the drug reservoir 230.

Figure 4:
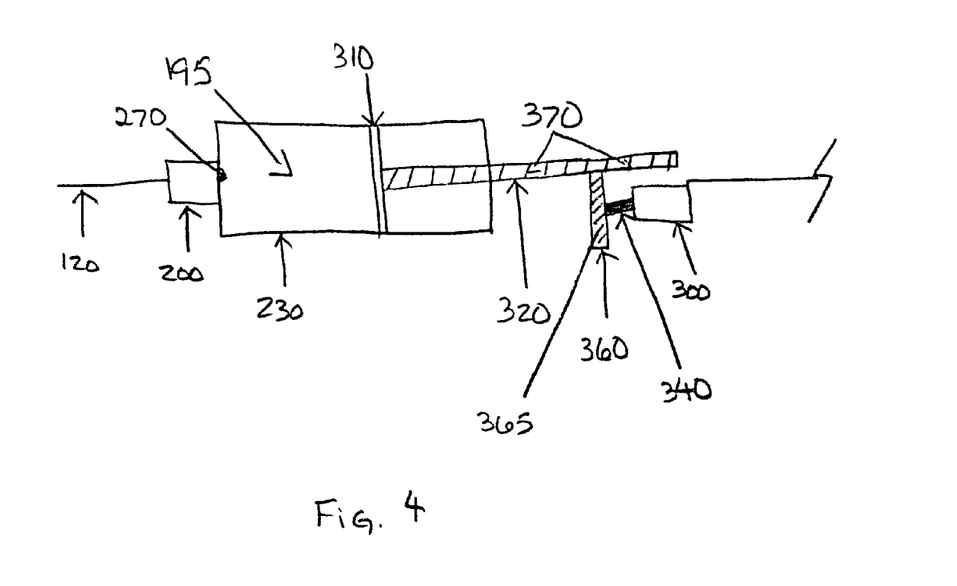
FIG. 4 illustrates the embodiment of FIG. 3 without an encasing endoscope or catheter.

FIG. 4 provides an enlarged view of the distal end of the embodiment depicted in FIG. 3 without the endoscope 140 or the encasing catheter 170. As is evident and as was illustrated in FIG. 3, the electric motor 300 has a motor shaft 340 that is in direct rotational communication with a gear 360 that is in direct rotational communication with the screw threads 370 of the connecting member 320. As the electric motor 300 turns it rotates the motor shaft drive 340 that turns the gear 360 which is inscribed with teeth 365 that meet with and advance the screw threads 370 thereby rotating and advancing the connecting member 320. As in FIG. 3, the connecting member 320 advances and pushes the piston 310 further into the drug reservoir 230 thereby forcing any drug 195 present in the drug reservoir 230 out the exit orifice 270, through the connection tube 200, and out the hypodermic needle 120.

Figure 5:
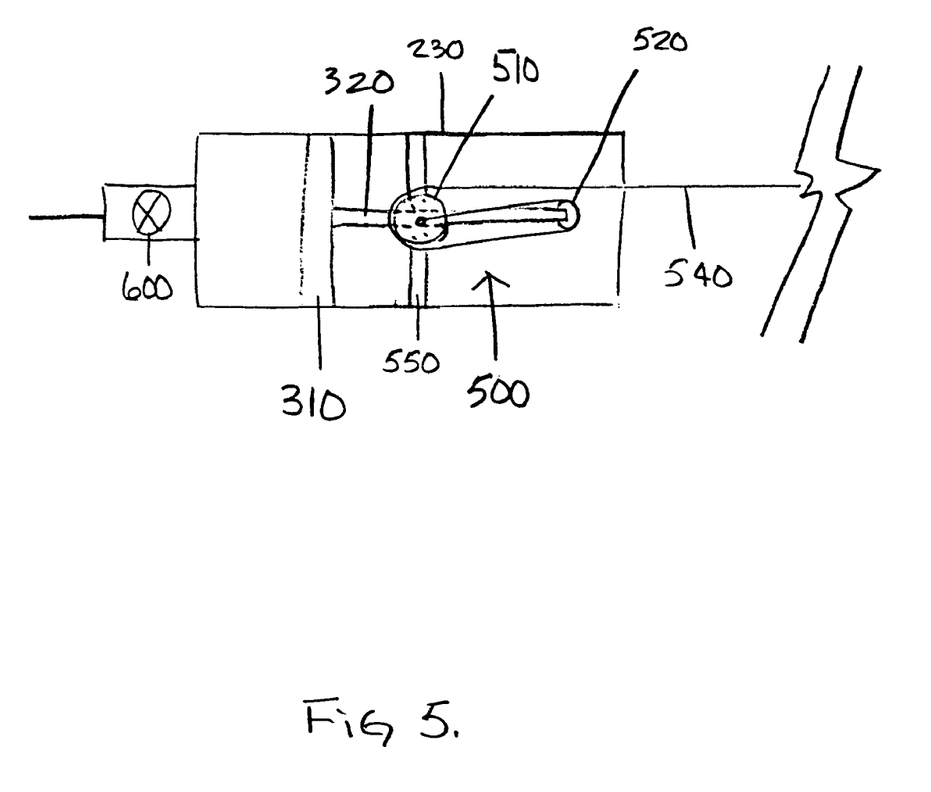
FIG. 5 illustrates an alternative embodiment, without an encasing catheter or endoscope, that utilizes a cable assembly to assist in the delivery of the drug in accordance with the present invention.

Alternatively, instead of using the electric motor assembly described above, a cable assembly system could be used to force the drug 195 from the drug reservoir 230. FIG. 5, which provides an enlarged view of the distal end of the present invention, without the encasing endoscope or catheter, employs such a cable assembly system 500. The cable assembly system shown in FIG. 5 contains a piston 310, a connecting member 320 perpendicularly affixed to the piston 310, a first pulley 520, rotatably attached to the end opposite the piston 310 of the connecting member 320, a second pulley 510, rotatably connected to a support bar 550 that is rigidly connected to the drug reservoir 230, and a cable 540. The cable assembly system, as is evident, also contains a cable 540. One end of the cable 540 is attached to the center of the second pulley 510 with the other end being free and accessible at the proximal end of the drug delivery device. The cable 540 loops around the first pulley 520, around the second pulley 510 and then extends though the drug delivery device 260 until the cable's other end emerges at the device's proximal end for use by the Endoscopist.

As required, the Endoscopist will pull on the loose available end of the cable 540 in order to inject the drugs into the luminal area to be treated. In operation, when the cable 540 is pulled the first pulley 520 is drawn towards the second pulley 510. Being coupled to the connecting member 320, the first pulley 520 moves the connecting member 320 along with it. As the first pulley 520 moves closer to the second pulley 510, which is rotatably mounted to the support member 550, the connecting member 320 and the piston 310, connected to the first pulley 520, will also move the same distance. As the piston 310 moves, the drug 195 present in the drug reservoir 230 is urged therefrom and is ultimately forced out the hypodermic needle into the luminal area to be treated. As is evident the cable can be pulled at various rates of speed and for various predetermined distances in order to control the dosage delivered. Therefore, in practice, the Endoscopist can administer a portion of the drugs present in the drug reservoir or can displace the entire volume of the drug reservoir by varying the length of cable 540 that the Endoscopist pulls from the working end of the drug delivery device 260.

Figure 6A:
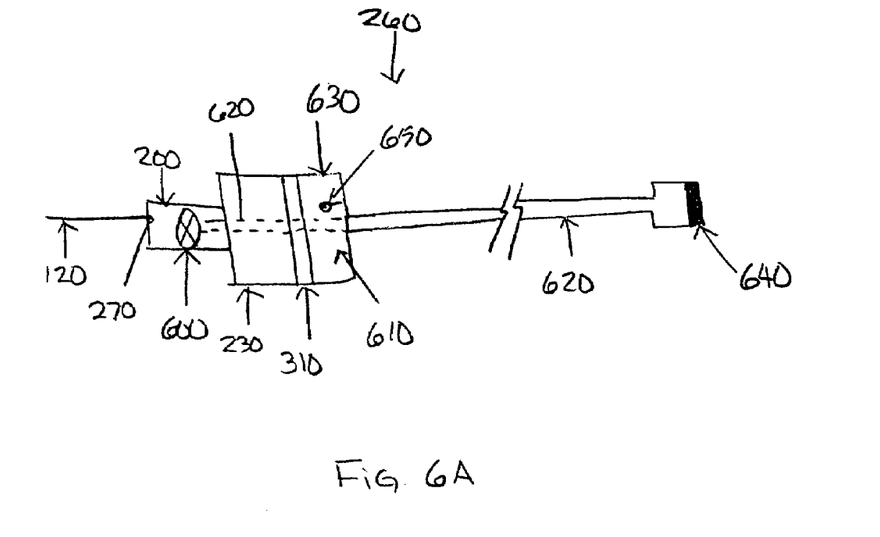
FIG. 6A illustrates an alternative embodiment, without an encasing catheter or endoscope, that utilizes compressed gas to assist in the delivery of the drug in accordance with the present invention.

FIG. 6A is a view of the distal end of another embodiment of the present invention absent the encompassing catheter 170 and the endoscope 140. In this embodiment compressed gas is utilized to move piston 310 instead of an electric motor or cable assembly system. The compressed gas 610 is located within a compressed gas chamber 630 proximate to the piston 310 of the drug reservoir 230 and is used to generate the compressive force required to push the piston 310 against the drug 195 and to force the drug 195 through the exit orifice 270. The compressed gas 610 may be pre-loaded into the compressed gas chamber 630 before the entire drug delivery device 260 is inserted into the patient. Various methods of loading the compressed gas 610 into the compressed gas chamber 630 will be readily apparent to one of skill in the art and can include pre-loading both the compressed gas 610 and the drug 195 before the procedure is performed at the manufacturing facility, and loading the compressed gas 610 into the compressed gas chamber 630 through a charging orifice 650 contemporaneous with the performance of the procedure.

Figure 6B:
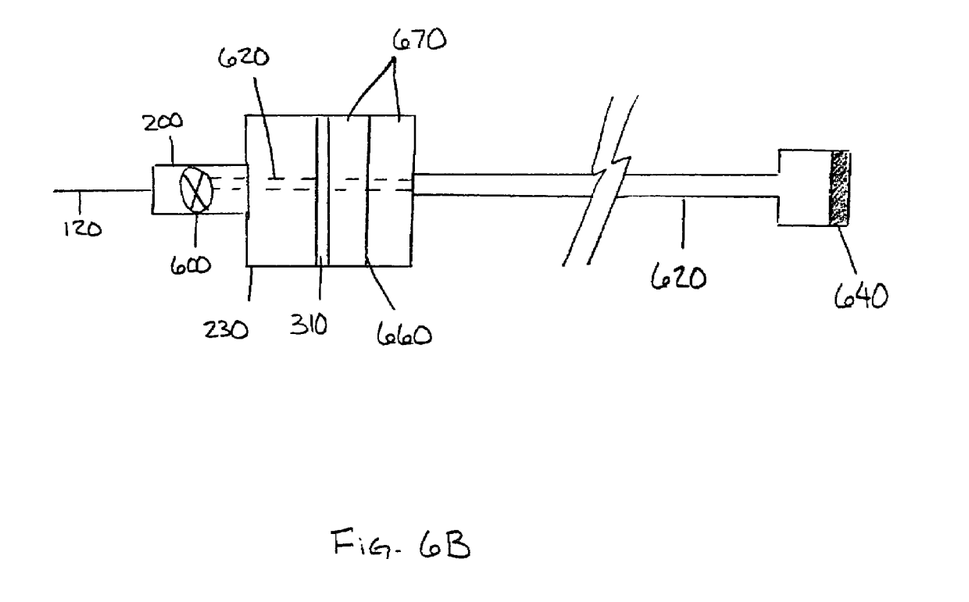
FIG. 6B illustrates an alternative embodiment, without an encasing catheter or endoscope, that utilizes two reactive chemicals to generate the compressed gas that assists in the delivery of the drug in accordance with the present invention.

Alternatively, as can be seen in FIG. 6B, instead of loading compressed gas into compressed gas chamber 610 the compressed gas chamber may be divided by a removable partition 660 that separates two reactive chemicals 670 which, when combined, react to create an innocuous compressed gas. Therefore, in practice, before the beginning of the procedure, the Endoscopist will remove the removable partition 660, from the compressed gas chamber, exposing the reactant chemicals to each other and causing them to react and generate the compressed gas that will be required to eject the drug 195 from the drug reservoir 230.

To prevent the undesired discharge of the drug 195 once the compressed gas chamber is charged a micro-valve 600 is inserted into the connection tube 200. This micro-valve 600 is opened and closed by depressing a plunger 640 located at the proximal end of the drug delivery device 260 on the proximal end of the valve control line 620, outside the patient's body. The valve control line 620 is in communication with the micro-valve 600. When the plunger 640 is depressed it pushes a cable 660, located within the valve control line 620 that slides the micro-valve 600 open. When the micro-valve 600 is opened the drug 195, under pressure from the compressed gas 510, can now flow and travel through the micro-valve 600 and out the hypodermic needle 120. Thus, as required during the procedure, the Endoscopist will depress the plunger 640, which opens the micro-valve 600 and permits the compressed gas 610 to push the piston 310 against the drug 195 in order to urge the drug out of the reservoir and ultimately into the treatment area.

In an alternative embodiment of the device in FIG. 6A, the drug reservoir 230 is, instead, manufactured as a reconfigurable chamber. Made from a flexible membrane, in lieu of the rigid material depicted above, the reconfigurable chamber collapses from the compressive loads of the compressed gas during use. Rather than pushing the piston 310 to force the drug 195 from the drug reservoir 230 the compressed gas 610 would act upon the reconfigurable drug reservoir 230 to collapse it and squeeze the drugs from it once the micro-valve 600 is opened.

Figure 7:
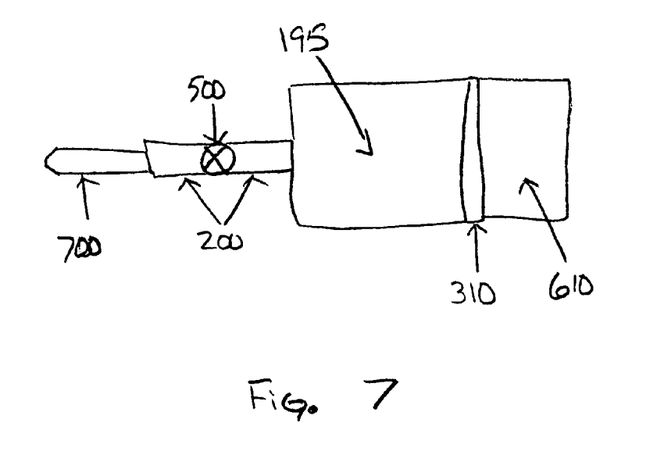
FIG. 7 illustrates an alternative embodiment of FIG. 6A wherein an injection nozzle, instead of a hypodermic needle, is utilized to administer the drug.

FIG. 7 is an alternative embodiment of FIG. 6A illustrating an injection nozzle 700 being employed for injecting drugs 195 into the treatment area 110 in lieu of a hypodermic needle 120. The injection nozzle, as is known to one of skill in the art, drives the drug into the tissue.

Figure 8:
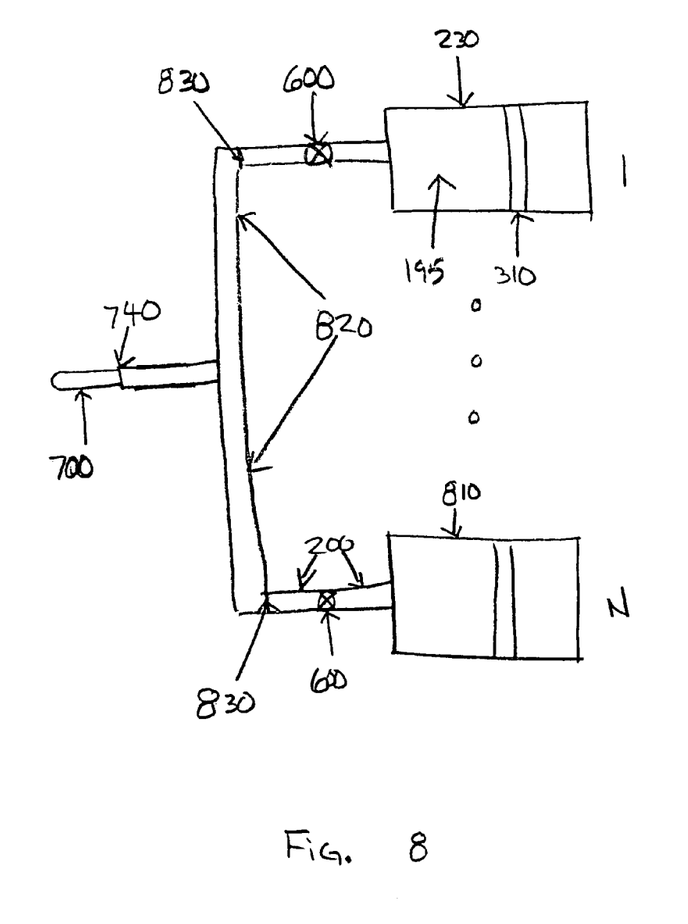
FIG. 8 illustrates an alternative embodiment of FIG. 7 that employs multiple drug reservoirs manifolded together to a single injection nozzle.

FIG. 8 illustrates an alternative embodiment of the present invention which employs a plurality of N drug reservoirs at the distal end of the drug delivery device and an injection nozzle 700. As is evident several drug reservoirs 230 and 810 numbered 1 . . . N are connected to a manifold 820 with N input ports 830 and one output port 740. The output port 740 of the manifold 820 is connected to the injection nozzle 700. Different drugs can be loaded into each of the drug reservoirs to be injected one at a time or in different combinations into the manifold 820 and out the injection nozzle 700 of the drug delivery device. Alternatively, the same drug can be placed within each of the drug reservoirs to increase the dosage available for the procedure. Also visible in FIG. 8 are microvalves 600, hollow connection tubes 200, injecting drugs 195 within drug reservoir 230, and pistons 310.

As described above, an endoluminal drug delivery method device is provided. The disclosed embodiments are illustrative of the various ways in which the present invention may be practiced. Other embodiments can be implemented by those skilled in the art without departing from the spirit and scope of the present invention.

What is claimed is:

1. An endoluminal drug delivery device comprising:
   a catheter having a distal end for placement inside a patient's body and a proximal end for placement outside the patient's body;
   a drug reservoir located at said distal end of said catheter, the drug reservoir being fixed in the same position with respect to the distal end of the catheter during placement of the catheter inside the patient's body and during drug delivery, the drug reservoir having an interior surface, the interior surface of the drug reservoir being fluidly isolated from the proximal end of the catheter;
   a piston moveable within said drug reservoir;
   a motor having a shaft drive; and
   a connecting member having a first end and a second end
      said first end of said connecting member rotatably connected with said shaft drive of said motor and
      said second end of said connecting member rotatably connected with said piston.

2. The endoluminal drug delivery device of claim 1 wherein the motor is an electric motor with a rotating shaft drive.

3. The device of claim 1 wherein the motor is positioned within the catheter.

4. The device of claim 1 wherein a threaded connection removably links the reservoir and the catheter.

5. The device of claim 1 further comprising wires connecting the motor to a control switch positioned at the proximal end of the catheter.

* * * * *